United States Patent
Squires et al.

(10) Patent No.: US 8,945,225 B2
(45) Date of Patent: Feb. 3, 2015

(54) PROSTHETIC SPINAL DISC SYSTEM

(75) Inventors: Craig Squires, Cordova, TN (US);
Mark Dace, Collierville, TN (US);
Stanley Palmatier, Olive Branch, MS (US)

(73) Assignee: Warsaw, Orthopedic, Inc., Warsaw, IN (US)

( * ) Notice: Subject to any disclaimer, the term of this patent is extended or adjusted under 35 U.S.C. 154(b) by 948 days.

(21) Appl. No.: 12/505,756

(22) Filed: Jul. 20, 2009

(65) Prior Publication Data

US 2011/0015744 A1 Jan. 20, 2011

(51) Int. Cl.
*A61F 2/44* (2006.01)
*A61F 2/30* (2006.01)

(52) U.S. Cl.
CPC ....... *A61F 2/442* (2013.01); *A61F 2002/30014* (2013.01); *A61F 2002/30016* (2013.01); *A61F 2002/3008* (2013.01); *A61F 2002/30224* (2013.01); *A61F 2002/30245* (2013.01); *A61F 2002/30462* (2013.01); *A61F 2002/30578* (2013.01); *A61F 2002/444* (2013.01); *A61F 2220/0075* (2013.01); *A61F 2230/0069* (2013.01); *A61F 2230/0071* (2013.01); *A61F 2250/0018* (2013.01); *A61F 2250/0019* (2013.01); *A61F 2250/0098* (2013.01)
USPC ...................................... 623/17.16

(58) Field of Classification Search
CPC ............. A61F 2002/444; A61F 2/446; A61F 2002/4495
USPC ............................................ 623/17.11–17.16
See application file for complete search history.

(56) References Cited

U.S. PATENT DOCUMENTS

| 7,338,525 | B2 | 3/2008 | Ferree | |
|---|---|---|---|---|
| 2001/0027343 | A1* | 10/2001 | Keller | 623/11.11 |
| 2006/0058881 | A1* | 3/2006 | Trieu | 623/17.16 |
| 2006/0129242 | A1* | 6/2006 | Bergeron et al. | 623/17.16 |
| 2006/0149380 | A1* | 7/2006 | Lotz et al. | 623/17.12 |
| 2007/0168042 | A1* | 7/2007 | Hudgins et al. | 623/17.16 |
| 2009/0326580 | A1* | 12/2009 | Anderson et al. | 606/246 |

FOREIGN PATENT DOCUMENTS

WO 2004052247 A1 6/2004

\* cited by examiner

*Primary Examiner* — Matthew Lawson

(57) ABSTRACT

A prosthetic spinal disc system is provided. The prosthetic disc system has a nucleus component having an upper surface configured to engage a superior vertebra and a lower surface configured to engage an inferior vertebra, an anchor configured to affix to an anterior surface of at least one of the superior vertebra or the inferior vertebra, and a tether tying the nucleus component to the anchor. In such embodiments, the nucleus component further has a perimeter situated substantially between the upper surface and the lower surface of the nucleus component and the tether is at least partially situated on the perimeter of the nucleus component. In certain embodiments, the upper surface and the lower surface of the nucleus component are configured to allow for implantation of the disc system such that after a discectomy, no preparation of at least one of the superior and inferior vertebrae is necessary.

20 Claims, 9 Drawing Sheets

PROSTHETIC SPINAL DISC SYSTEM

FIELD OF INVENTION

The present invention is directed to prosthetic implants for replacing intervertebral discs or nuclei of the spine, and systems and methods for implanting such prosthetic implants.

BACKGROUND

The present disclosure relates generally to devices and methods for relieving disc degeneration or injury, and more particularly, to devices and methods for augmenting or replacing a nucleus pulposus. Within the spine, the intervertebral disc functions to stabilize and distribute forces between vertebral bodies. The intervertebral disc has a nucleus pulposus which is surrounded and confined by the annulus fibrosis (or annulus).

Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, preventing the degenerated disc from maintaining the normal separation of vertebral bodies.

The interior portions of intervertebral discs of the spine are not provided with a significant blood supply by the body. Their homeostasis is aided by the diffusion of fluids into the disc tissue, thus supplying them with nutrients. This, to some extent, allows the tissue to grow and repair damage done by stress as the intervertebral joint moves. Despite this process, in mature adults, spinal disc tissue degrades continuously over time. Degenerative disc disease typically results from the normal aging process, in which the tissue gradually loses its natural water and elasticity, causing the degenerated disc to shrink. Sufficiently advanced degeneration can lead to herniation or rupture of the spinal disc. In addition to normal wear and tear, herniated discs can occur from exceptional strain or trauma.

Herniation of a spinal disc can result in a number of debilitating symptoms, including intractable pain, weakness, and sensory loss. Treatment of these symptoms frequently requires surgical removal of at least a portion of the herniated disc, a procedure known as discectomy. Often, discectomy alone cannot stop the progressive degeneration at the level of disc excision. An additional procedure often is performed in conjunction with the discectomy with the objective of fusing together the vertebral bodies surrounding the affected disc space. This is accomplished by removing the cartilaginous portion of the endplates by scraping the surfaces of the vertebral body and inserting a piece of graft bone, which may be an allograft from a bone bank, or an autograft, typically taken from the iliac crest of the patient, or other suitable material.

Fusion procedures, however, can be problematic. Even when successful, the grafting or fusion procedure requires considerable recovery time before fusion is complete. Perhaps even greater concern, fusion procedures eliminate normal spinal biomechanics. Range of motion at the level of the fusion typically is eliminated because the affected vertebrae have been effectively joined to form a single bone structure. Because the patient tries to maintain the same overall range of motion of the entire spine, additional stress is imposed on the intervertebral discs of the adjacent vertebrae. This, in turn, may lead to accelerated degeneration at levels above and below the fusion site, which may require additional treatment, including discectomy and fusion at those adjacent levels. Additionally, grafting procedures carry some risk of tissue rejection and disease transmission if an allograft is used, and risk of harvest site morbidity when the patient's own tissue is used.

As a result of these difficulties with intervertebral fusion, attempts have been made to provide a prosthetic solution to degenerative disc disease that maintains the patient's normal spinal biomechanics, allows for shorter recovery times, and avoids the complications inherent in harvesting and/or grafting bone tissue.

Design and construction of such an implant, however, is not simple. Desirably, the implant should be precisely placed in a prepared intervertebral space, and should contain elements that are immobilized with respect to each of the vertebral bodies, so that the implant does not migrate or shift, potentially contacting, abrading, or otherwise damaging the spinal cord, ligaments, blood vessels, and other soft tissue. At the same time, the implant should allow the vertebral bodies to move relative to each other in a way that provides the equivalent motion afforded by a healthy intervertebral disc, and that allows the affected vertebral joint to participate in the coordinated overall movement of the spine in a way that closely approximates the natural movement of a healthy spinal column. The implant should be biocompatible, and avoid the introduction of toxic or harmful components into the patient, such as release of wear debris. The implant also should restore normal disc height and maintain the patient's vertebral lordosis, and should not allow any significant postoperative subsidence (protrusion or movement of the disc into the adjacent vertebral bodies) or expulsion (protrusion or movement of the disc outside of the disc space). The implant should be at least partially constrained by soft tissue in and around the intervertebral space, in order to allow a simpler, more efficient design. Further, such an implant also should ideally provide elasticity and dampening sufficient to absorb shocks and stresses imposed on it in a manner similar to that of the natural spinal disc.

In addition to the above requirements, there remains a need for a device which would decrease patient recovery time, and reduce the occurrence of postoperative degeneration at levels above and below the implant, as compared with fusion devices and techniques as well as existing motion-preserving devices. There also is a need for a device that does not require any significant preparation of the disc space prior to implantation. That is, some existing devices require significant shaping of the vertebral endplates prior to implantation for proper placement of the device. It is, therefore, desirable to provide a device that maintains motion and requires relatively little or no shaping of the endplates prior to implantation. It is desirable, however, for the same device to maintain proper positioning inside the disc space, restoring normal disc height and maintaining the patient's vertebral lordosis, lessen the chances for post-operative subsidence or expulsion, create relatively little or no wear debris, and provide elasticity and dampening sufficient to absorb shocks and stresses imposed on it in a manner similar to that of the natural spinal disc. Satisfying these requirements will provide a very high quality disc that also is easy to implant.

SUMMARY OF THE INVENTION

A prosthetic spinal disc system is provided. The prosthetic disc system has a nucleus component having an upper surface configured to engage a superior vertebra and a lower surface configured to engage an inferior vertebra, an anchor configured to affix to an anterior surface of at least one of the superior vertebra or the inferior vertebra, and a tether connecting the nucleus component to the anchor. The nucleus component further has a recess situated substantially between the upper surface and the lower surface of the nucleus component, and at least part of the tether is configured to be situated in the recess on the nucleus component.

In some embodiments of the prosthetic disc system of the present invention, the upper surface of the nucleus component has a convex shape. In certain embodiments of the prosthetic disc system of the present invention, the lower surface of the nucleus component has a convex shape. In some embodiments of the prosthetic disc system of the present invention, the upper surface of the nucleus component has a convex shape and the lower surface of the nucleus component has a convex shape.

In certain embodiments of the prosthetic disc system of the present invention, the nucleus component has a generally elliptical cross-sectional shape in a sagittal plane. In some embodiments of the prosthetic disc system of the present invention, the nucleus component has a generally circular cross-sectional shape in a transverse plane. In some embodiments of the prosthetic disc system of the present invention, the nucleus component has a generally elliptical cross-sectional shape in a sagittal plane and a generally circular cross-sectional shape in a transverse plane. In some embodiments of the prosthetic disc system of the present invention, the nucleus component has, at least in part, a generally circular cross-sectional shape in a sagittal plane.

In some embodiments of the prosthetic disc system of the present invention, the nucleus component has a center and an outer portion adjacent the recess, and when viewed in a sagittal plane, the nucleus component has a larger profile in its center than it has at the outer portion. In some of such embodiments, the nucleus component has a central portion located about the center of the nucleus, wherein the central portion is harder than the outer portion. In certain embodiments of the prosthetic disc system of the present invention, the nucleus component has a central portion and an outer portion adjacent the recess, wherein the central portion is harder than the outer portion.

In some embodiments of the prosthetic disc system of the present invention, the tether contains at least some flexible material. In some embodiments of the prosthetic disc system of the present invention, the anchor contains at least some flexible material.

In certain embodiments of the prosthetic disc system of the present invention, the tether is connected to the anchor at a central location. In some embodiments of the prosthetic disc system of the present invention, the recess is a concavity situated on an outer perimeter of the nucleus component.

In some embodiments of the prosthetic disc system of the present invention, the prosthetic disc system has a nucleus component having an upper surface configured to engage a superior vertebra and a lower surface configured to engage an inferior vertebra, and an anchor component connecting the nucleus component to at least one of the superior vertebra or inferior vertebra. In such embodiments, the nucleus component further has a recess situated substantially between the upper surface and the lower surface of the nucleus component, and at least part of the anchor component is configured to be situated in the recess on the nucleus component.

In certain embodiments of the prosthetic disc system of the present invention, the upper surface and the lower surface of the nucleus component are configured to allow for implantation of the disc system, after a discectomy, with no preparation of at least one of the superior and inferior vertebrae.

In some embodiments of the prosthetic disc system of the present invention, the prosthetic disc system has a nucleus component having an upper surface configured to engage a superior vertebra and a lower surface configured to engage an inferior vertebra, an anchor configured to affix to an anterior surface of at least one of the superior vertebra or the inferior vertebra, and a tether tying the nucleus component to the anchor. In such embodiments, the nucleus component further has a perimeter situated substantially between the upper surface and the lower surface of the nucleus component and the tether is at least partially situated on the perimeter of the nucleus component. In some of such embodiments of the prosthetic disc system of the present invention, the nucleus component further has a hole extending from a first point on or adjacent its perimeter that is near the anchor to a second point on or adjacent its perimeter substantially opposite the first point, and the tether extends from the anchor, through the hole, to the second point. In some of such embodiments, the prosthetic disc system of the present invention further has a locking mechanism affixed to the tether at the second point that maintains the tether in place on or adjacent the second point.

Additional aspects and features of the present disclosure will be apparent from the detailed description and claims as set forth below.

DETAILED DESCRIPTION

Figure 1:
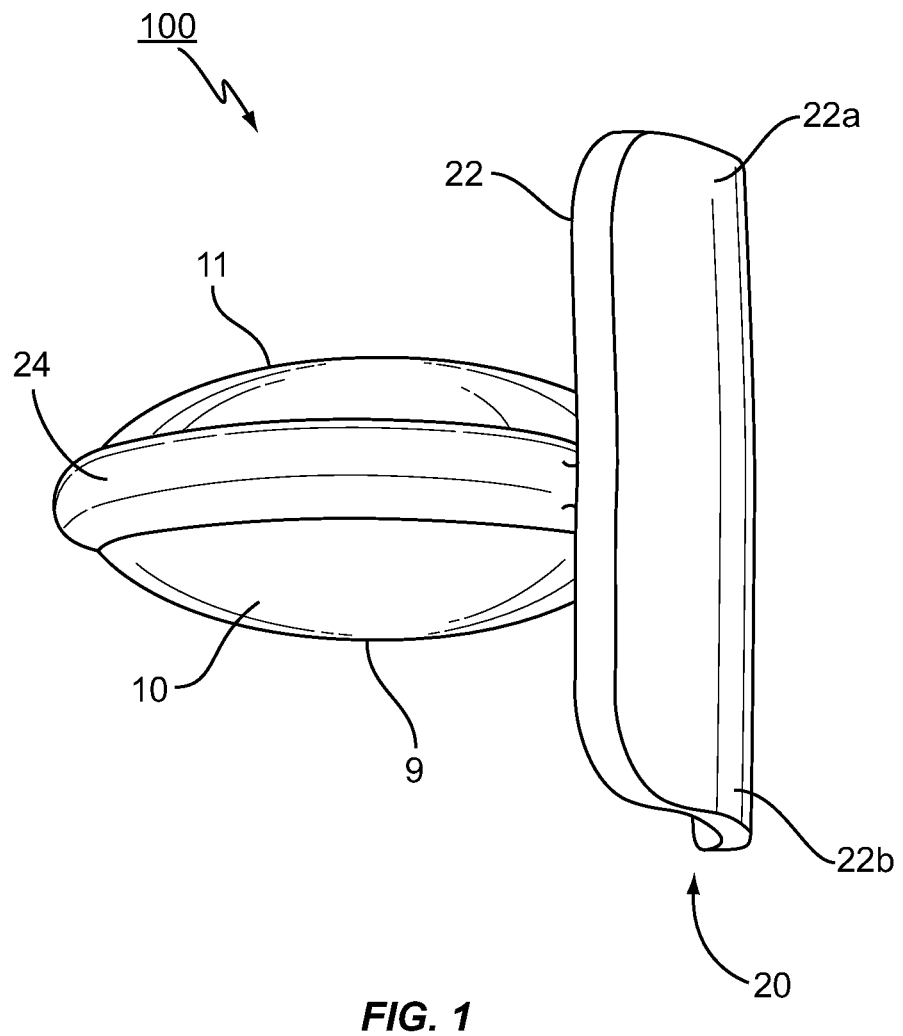
FIG. 1 is an isometric view of a prosthetic spinal disc system according to the present invention.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a prosthetic spinal disc system 100 according to the present invention. The disc system 100 has a nucleus component 10 and a flexible anchor component 20. The nucleus component 10 has an upper surface 11 configured to engage a superior vertebra and a lower surface 9 configured to engage an inferior vertebra. The anchor component 20 is configured to affix to an anterior surface of at least one of the superior vertebra or inferior vertebra, and has an anchor 22 and a tether 24. The tether 24 is a ring or band of material 24. It is desirable for at least one of the anchor 22 or the tether 24 to have a certain degree of flexibility. In some embodiments, the anchor 22 is a tension band or plate made of a flexible material, but can be any type of plate. For example, a plate that allows for translation in two directions also will work with the present invention.

Figure 1A:
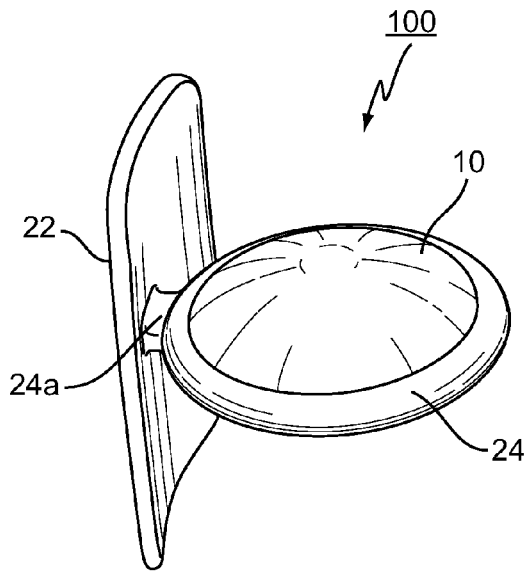
FIG. 1A shows an isometric view of the prosthetic disc system of FIG. 1.
Figure 1B:
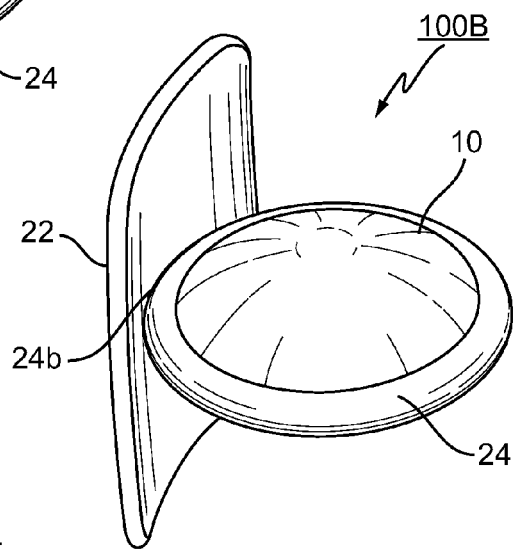
FIG. 1B shows an isometric view of another embodiment of a prosthetic disc system according to the present invention.
Figure 1C:
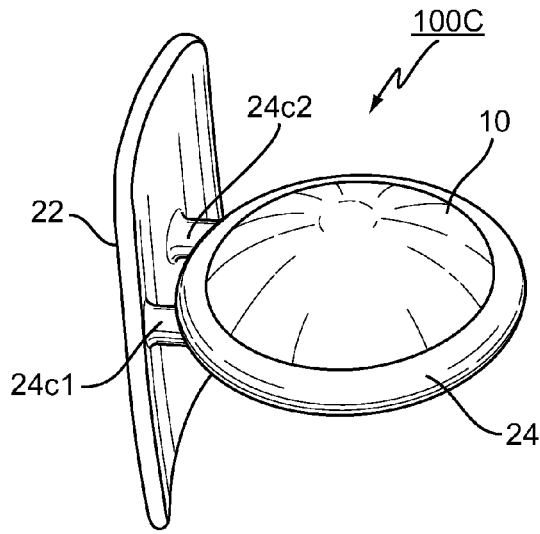
FIG. 1C shows an isometric view of another embodiment of a prosthetic disc system according to the present invention.

According to the invention, once implanted, the nucleus component 10 is intended to reside inside the disc space between two adjacent vertebrae, while the anchor 22 of the anchor component 20 is intended to affix to the vertebrae. As shown in the embodiment of FIG. 1, the nucleus component 10 is bound around its perimeter by the tether 24, which is attached to the anchor 22. Thus, a feature of the present invention is that the nucleus component 10 is tethered or tied to the anchor 22. FIG. 1A shows another view of the prosthetic disc system 100 of FIG. 1. As shown, the tether 24 also has a relatively short length of material or leg 24a that aids the tether 24 in connecting the nucleus component 10 to the anchor 22. This leg 24a also can be used to help with proper placement of the nucleus component 10, and in doing so, serves one purpose of providing a distance between the anchor 22 and the nucleus component 10. That is, if the leg 24a is longer than a given distance, then the nucleus component 10 is situated more posteriorly in the disc space. FIG. 1B shows another embodiment of the prosthetic disc system 100B of the present invention, where if relatively no additional distance is desired, tether 24 may attach directly to the anchor 22, for example, at point 24b. Further, FIG. 1C shows yet another embodiment of a prosthetic disc system 100C of the present invention, depicting another manner of connecting the nucleus component 10 to the anchor 22. In particular, in embodiment 100C, the tether 24 connects to the anchor 22 by means of a plurality of attachment points. Specifically, as shown in FIG. 1C, there are two legs 24c1 and 24c2 extending from the tether 24 connecting the nucleus component 10 to the anchor 22. In all the embodiments of FIGS. 1, 1B and 1C, the flexibility of the tether 24 may be provided by the part of the tether 24 surrounding the perimeter of the nucleus component 10 or may be provided by a distinct length, portion of material or leg (for example, 24A, 24c1, or 24c2) or both. The anchor 22 may be a tension band, flexible plate, flexible flaps, or tabs, which is then anchored to the vertebral bodies by any known means, such as screws, staples, adhesive, or other mechanisms. The tether 24, when flexible, allows the nucleus component 10 to move as necessary to achieve physiologic spinal motion, but prevents the nucleus component 10 from migrating beyond desired limits. In the embodiments of FIGS. 1, 1B and 1C, the anchor 22 and the tether 24 of anchor component 20 are both made of non-resorbable material so that they can continue to perform their respective functions indefinitely.

In the previously-described embodiments, the nucleus component 10 has a generally elliptical cross-sectional shape in both the sagittal or coronal planes (when viewed from the side), and has a generally circular shape (or cross section) in the transverse plane (when viewed from above). The respective shapes of the flexible anchor component 20 and the nucleus component 10, however, can vary. For example, in the transverse plane, the nucleus component 10 can be round, oval, square, trapezoidal or another shape. When the nucleus component 10, however, has an elliptical cross-sectional shape (when viewed in the sagittal plane) as shown in FIG. 1, the device provides for easy articulation, and translation of the adjacent vertebral bodies. Further, an elliptical shape (and particularly, when also having a generally circular cross-sectional shape in the transverse plane) provides a significant amount of surface area for contacting the adjacent vertebrae. A larger surface area that closely resembles the part of the vertebrae that the nucleus component 10 is contacting helps distribute compressive forces over a wider area than if the nucleus component 10 had less surface area to contact the adjacent vertebrae. In yet other embodiments, the nucleus component 10 has a complex geometry similar to that of the natural anatomy of the mating vertebral bodies. Further, with the present invention, it is intended that little or no endplate preparation (for example, shaping, contouring, or milling of the endplates of the adjacent vertebrae) be needed, so as to retain as much bone as possible, and so as to make implantation relatively simple and requiring fewer steps.

With the proper shape and materials of the nucleus component 10, the prosthetic disc system of the present invention also provides the ability to restore disc height, and maintain decompression of the adjacent vertebral bodies between which it is intended to serve as a prosthetic disc. The nucleus component 10 can be made from metal, polymer, ceramic, or other biocompatible material as desired. The anchor 22 and tether 24 can be made of all the same material, or a combination, chosen from, for example, solid polymer, fabric, metal mesh, or other material. One aspect of the present invention is that there is flexibility between the nucleus component 10 and the anchor component 20. In this way, it is intended that the material used for the tether 24 remain flexible indefinitely in order to preserve motion and proper functioning of the disc system of the present invention. In some embodiments, the nucleus 10 is made from Ultra High Molecular Weight Polyethylene ("UHMWPE"), and the tether 24 is made from braided or woven UHMWPE fabric.

Figure 2:
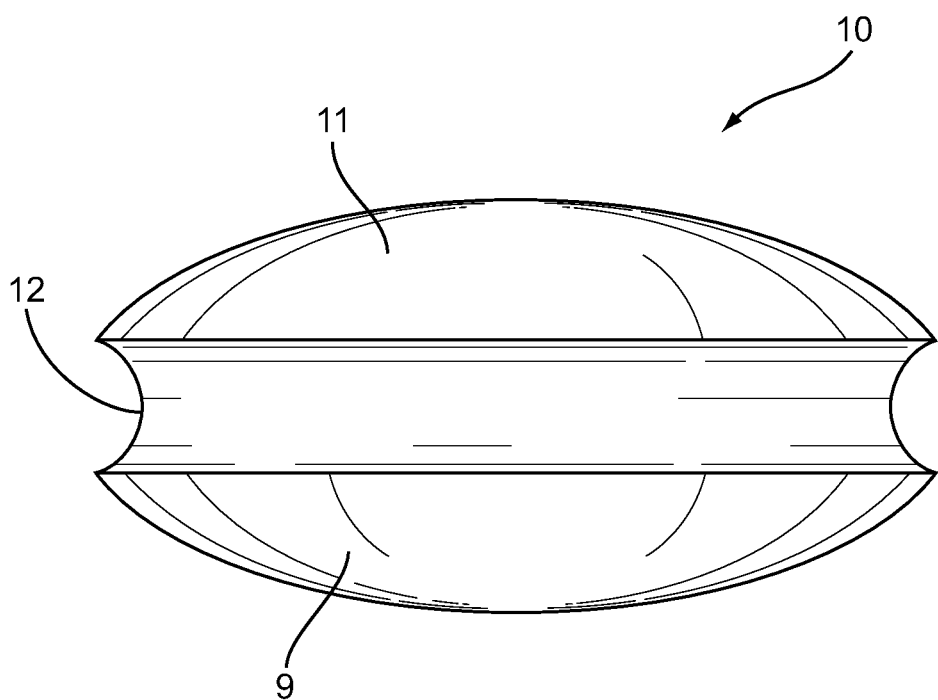
FIG. 2 shows a side view of a nucleus component of the prosthetic disc system of FIG. 1.

FIG. 2 shows a side view of a nucleus component 10 according to the present invention. In particular, FIG. 2 depicts a channel 12 on the nucleus component 10 that is designed for retaining the tether 24. The channel 12 may be described as a recess situated about the perimeter of the nucleus component 10. In general, the channel 12 is situated substantially between an upper surface 11 and a lower surface 9 of the nucleus component 10. As shown in FIG. 2, the channel 12 (or recess) has a generally semi-circular cross-sectional shape in the sagittal plane. In general, the channel 12 is a concavity situated on an outer perimeter (or outermost perimeter) of the nucleus component 10. As shown in FIG. 1, the tether 24 has a generally circular cross-section that matingly engages with the channel 12. Note, however, that the channel 12 and corresponding tether 24 may have different shapes, for example, both may have a substantially rectangular-shaped cross section. As opposed to material that may fully encompass the nucleus component 10, the tether 24 and the associated channel 12 of the present disc system 100 allows for increased flexibility or adjustability. Further, such arrangement allows for relatively simple manufacture and a secure engagement of the nucleus component 10 to the anchor 22.

Figure 3:
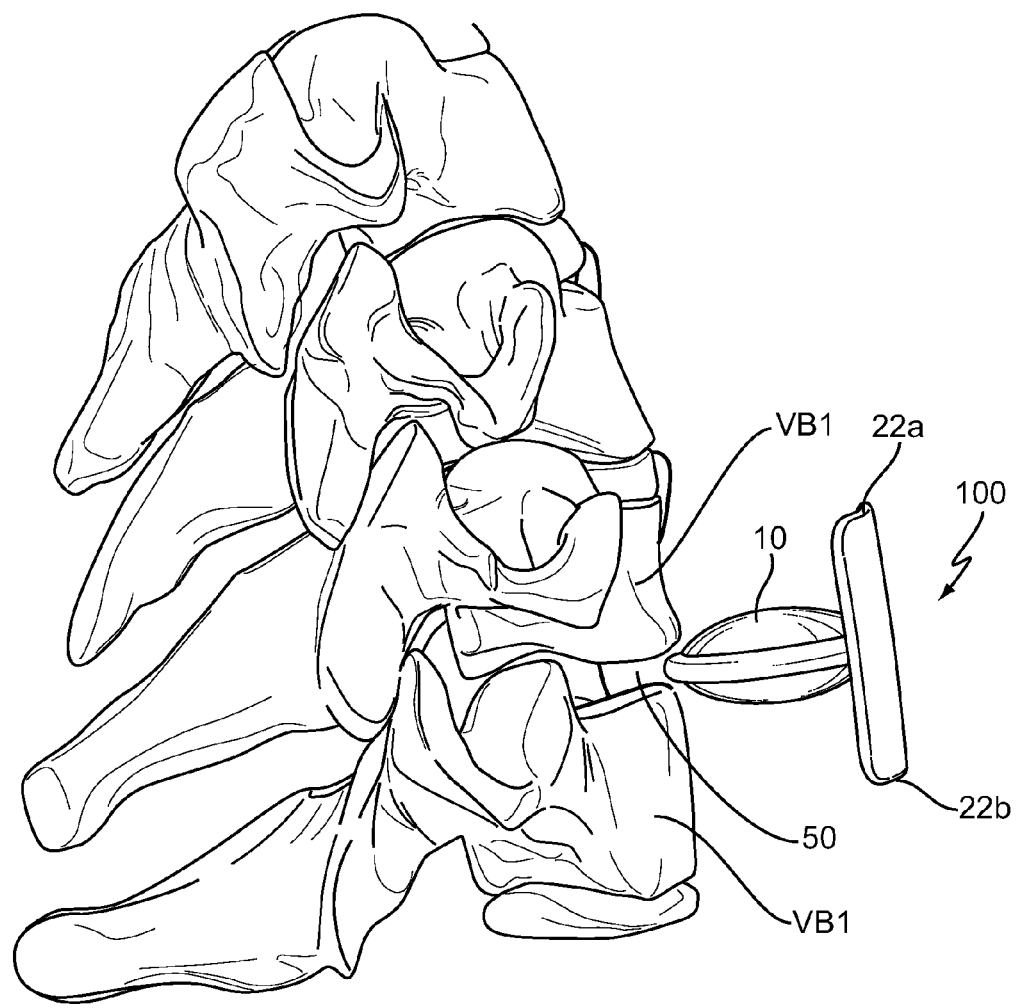
FIG. 3 shows an isometric view of a segment of vertebral where the prosthetic disc system of FIG. 1 may be utilized.

FIG. 3 shows a segment of vertebral column, and in particular, where the prosthetic disc system 100 of the present invention may be utilized. Specifically, FIG. 3 shows the disc system 100 just prior to implantation in the disc space 50 between vertebral bodies VB1 and VB2. After a discectomy is performed between vertebral bodies VB1 and VB2, the prosthetic disc system 100 may be implanted so that the nucleus component 10 and tether 24 occupy the resulting disc space 50. Alternatively, some variation in the procedure and result may take place. For example, some part or all of the annulus may remain and such a space inside the annulus may accommodate the nucleus component 10 of the disc system 100 of the present invention.

Figure 4:
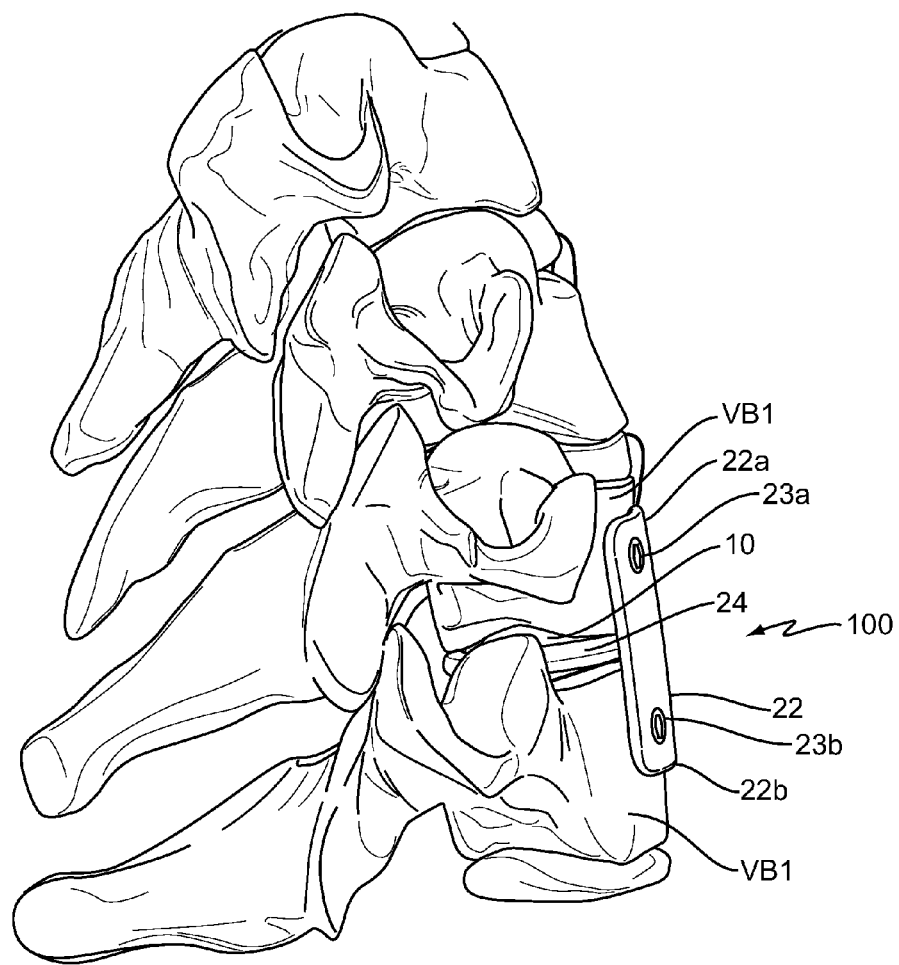
FIG. 4 shows an isometric view of the segment of vertebral column of FIG. 3 in cooperation with the prosthetic disc system of FIG. 1.

FIG. 4 shows the segment of vertebral column of FIG. 3 after the prosthetic disc system 100 has been implanted. As designed, the nucleus component 10 and tether 24 occupy the resulting disc space 50, and are intended to maintain the distance between endplates of vertebral bodies VB1 and VB2. The nucleus component 10 and tether 24 also are intended to allow the vertebral bodies VB1 and VB2 to move relative to each other in a way that provides the equivalent motion afforded by a healthy intervertebral disc, and that allows the affected vertebral joint to participate in the coordinated overall movement of the spine in a way that closely approximates the natural movement of a healthy spinal column. As shown in FIGS. 3 and 4, anchor 22 has a superior (or upper) portion 22a and an inferior (or lower) portion 22b. As shown, superior portion 22a of anchor 22 affixes to the anterior surface of superior vertebra VB1, whereas inferior portion 22b of anchor 22 affixes to the anterior surface of inferior vertebra VB2. The anchor 22, be it the superior portion 22a and inferior portion 22b or other portion or portions, can be affixed or anchored to the vertebral bodies VB1 and VB2 by any known means, such as screws, staples, adhesive, or other mechanisms. As shown in FIG. 4, screws 23a and 23b are used to affix portions 22a and 22b of anchor 22 to vertebrae VB1 and VB2, respectively. Screw holes to accommodate screws 23a and 23b may or may not be provided in anchor 22.

As shown with respect to the embodiment of the prosthetic disc system 100 of FIG. 1, the benefits of the tether 24, or the particular manner in which the nucleus component 10 is tethered to the anchor 22, are several. Any degree of flexibility in the tether 24 allows the nucleus component 10 to move as necessary to achieve physiologic spinal motion, but prevents the nucleus component 10 from migrating beyond desired limits. The manner of tethering allows for a central point or central location (as opposed to a length) of attachment of the nucleus component 10 to the anchor 22, i.e., at least with respect to embodiments 100 and 100B, and with similar embodiments according to the present invention where a central point of attachment is present. This single, central point of attachment (which is the point along the perimeter of the nucleus component 10 where the tether 24 is affixed to the anchor 22, as opposed to, e.g., a length) helps with rotation and angular movement of the nucleus component 10 relative to the adjacent vertebral bodies VB1 and VB2. The particular manner of placing the tether 24 around the perimeter of the nucleus component 10, and particularly, with use of the channel 12 of the nucleus component 10 allows for a relatively secure affixation of the two parts, while still achieving the movement benefits just described, and particularly, more flexibility and adjustability in the disc system 100 than existing prosthetic disc systems. Having the tether 24 on the perimeter of the nucleus component 10 does not subject the tether 24 (and its material) to heavy wear, limiting any amount of wear debris. For example, if a tether completely surrounded the nucleus component 10, then such a tether would not be subject to loads from the superior and inferior vertebral bodies and multi-directional forces from them, thereby potentially creating significant wear debris. Over time, that could create more and more wear debris and could damage the tether and its capability to function as intended would be lessened or destroyed. In addition, embodiments where the tether completely surrounds the nucleus could result in tissue growth in the area of and around the tether, which could lead to increased rigidity of the tether, more wear debris, subsequent damage to the tether and/or nucleus component, and potentially a lower range of motion or loss of motion.

Another feature of the present invention is that a radiographic marker can easily be incorporated into the disc system 100. That is, one or more radiographic markers may placed on or woven into the tether 24. Because the tether 24 is designed to be situated on the perimeter of the nucleus component 10, this location can easily be used to indicate positioning of the nucleus component 10 of the prosthetic disc system 100. When part of the disc system 100 is radiographic, such markers can be identified in x-ray or other imaging techniques to achieve desired positioning of the nucleus component 10. Another option to determine positioning is that other parts of the disc system 100 could have radiographic markers or be made of a radiographic material. For example, parts of the nucleus component 10 or the anchor 20, or these entire components may have radiographic markers or be made in part or entirely from radio-opaque material.

Figure 5:
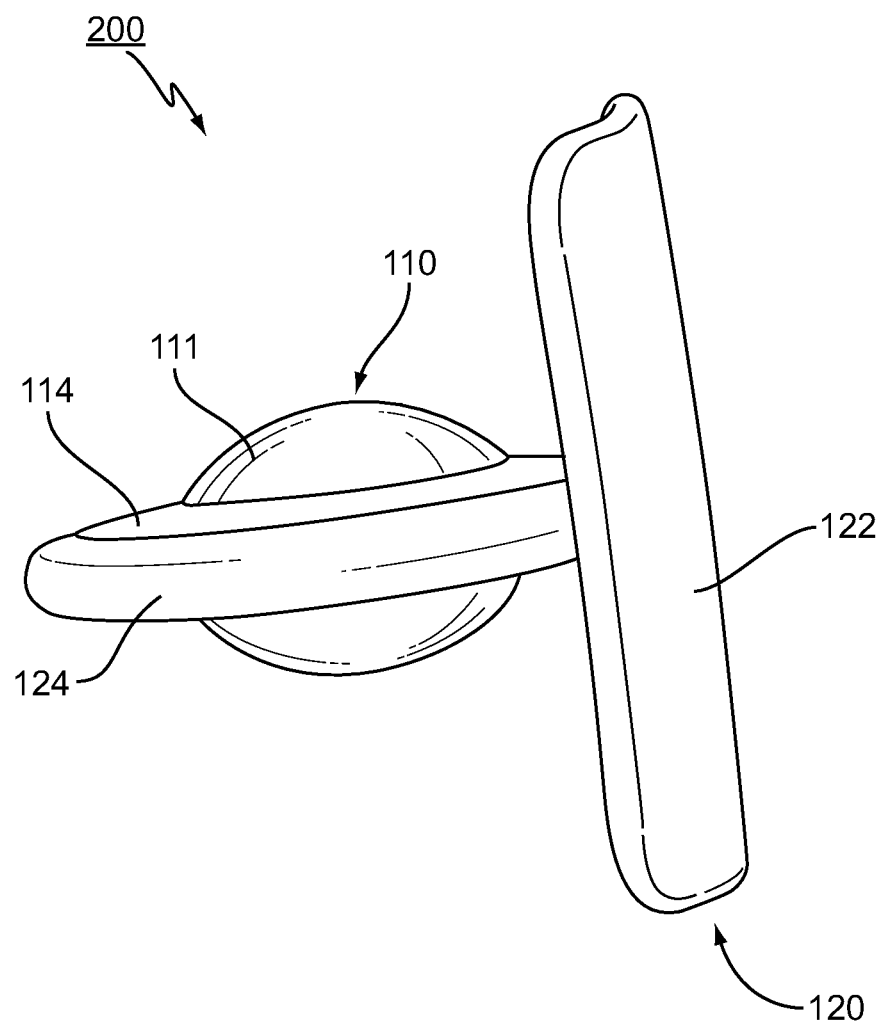
FIG. 5 shows an isometric view of another prosthetic spinal disc system according to the present invention.

FIG. 5 shows a prosthetic spinal disc system 200 according to the present invention. The disc system 200 has a nucleus component 110 and a flexible anchor component 120. The anchor component 120 has an anchor 122 and a tether 124, which similar to that of disc system 100, is a ring or band of material 124. It is desirable for at least one of the anchor 122 or the tether 124 to have a certain degree of flexibility. In some embodiments, the anchor 122 is a tension band or plate made of a flexible material.

As with prosthetic disc system 100, once implanted, the nucleus component 110 of disc system 200 is intended to reside inside the disc space between two adjacent vertebrae, while the anchor 122 of the anchor component 120 is intended to affix to adjacent vertebrae. As shown in the embodiment of FIG. 5, the nucleus component 110 is bound around its perimeter by the tether 124, which is attached to the anchor 122. Thus, as with prosthetic disc system 100, nucleus component 110 is connected to the anchor 122 by tether 124, and accordingly, has all of the accompanying benefits that the tether 124 provides. The anchor 122 and tether 124 of prosthetic disc system 200 can have the same variety in shape and materials as the counterpart features of prosthetic disc system 100 as long as it accomplishes the same desired functions.

Figure 6:
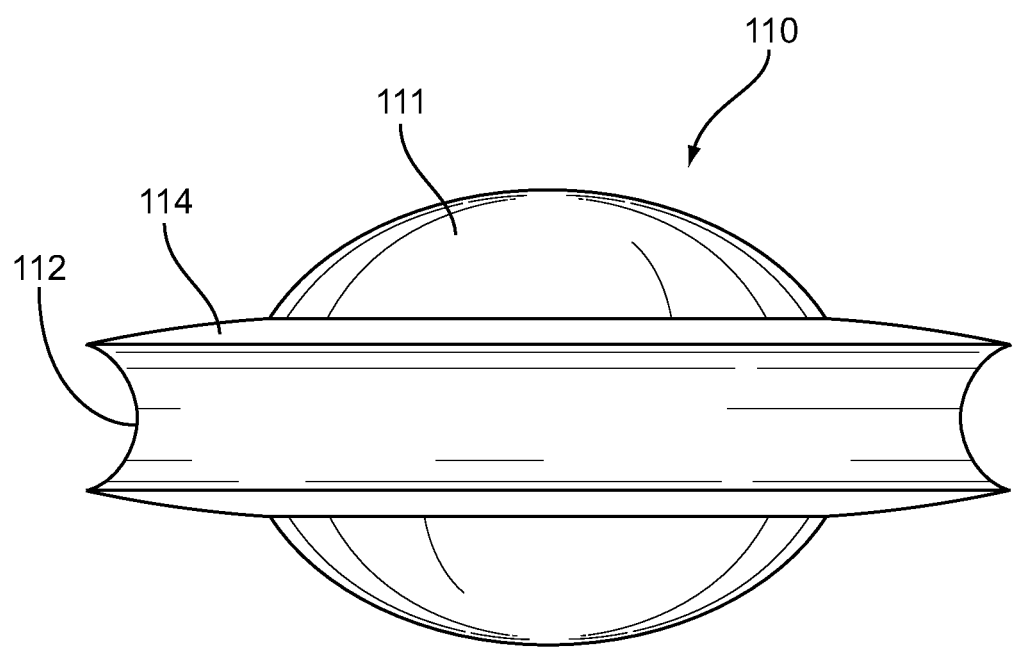
FIG. 6 is a side view of the nucleus component of the prosthetic disc system of FIG. 5.

Similarly, the nucleus component 110 may be made of a variety of materials, such as metal, polymer, ceramic, or other biocompatible material as desired. The shape of the nucleus component 110 also can vary, but as shown in FIG. 5, nucleus component 110 has a specific shape. That is, nucleus component 110 has a central portion 111 and an outer portion 114. As shown in FIG. 6, which is a side view of nucleus component 110, nucleus component 110 also has a channel 112 on the perimeter of outer portion 114 that is intended to serve the same purpose as that of channel 12 for prosthetic disc system 100.

As shown in FIGS. 5 and 6, the central portion 111 of nucleus component 110 has more of a curve or arc to its outer surface (when its cross section is viewed in the sagittal plane) than the outer portion 114 of nucleus component 110. In this way, the central portion 111 is thicker (or has more vertical height or a larger profile in the sagittal plane) than outer portion 114. As shown in FIGS. 5 and 6, the nucleus component 110 has a center (which generally is the center of the central portion 111) and an outer portion 114 adjacent a perimeter, and when viewed in a sagittal plane, the nucleus component 110 has a larger profile in its center than it has at the outer portion 114. With prosthetic disc system 200, it is intended that the thicker (or taller) central portion 111 supports the majority of the axial load experienced by disc system 200, whereas the outer portion 114 provides a progressive resistance to loads experienced when that portion of the spine undergoes flexion/extension and lateral bending motions. In this way, the outer portion 114 can act as a buffer to movement beyond the limits of the central portion 114 itself. In such an embodiment of the disc system 200 of FIGS. 5 and 6, the central portion 111 can be harder or stiffer than the outer portion 114. In addition, with materials having specific durometer levels, resistance to motion can be specifically tailored to the individual patient's needs. Regardless of the cross-sectional geometry of the nucleus component 110, the nucleus component 110 can be made from homogeneous material with a stiffness gradient (for example, hardest at the center, and gradually (or merely on a gradient) becoming softer approaching the perimeter), or a composite of components having different material characteristics as described above. For example, the central portion 111 composed of relatively hard material in combination with an outer portion 114 composed of relatively soft material. As these combinations or characteristics of the nucleus component 110 are exemplary, any combination or characteristics is contemplated within the spirit of the invention. For example, a disc system 200 having a central portion 111 composed of relatively soft material in combination with an outer portion 114 composed of relatively hard material may be more suitable to conform to the anatomic features of the endplates of the adjacent vertebrae. Another system 200 may include a combination of materials where the lower portion of the nucleus component 110 may have a different hardness level than the upper portion of the nucleus component 110.

Figure 7:
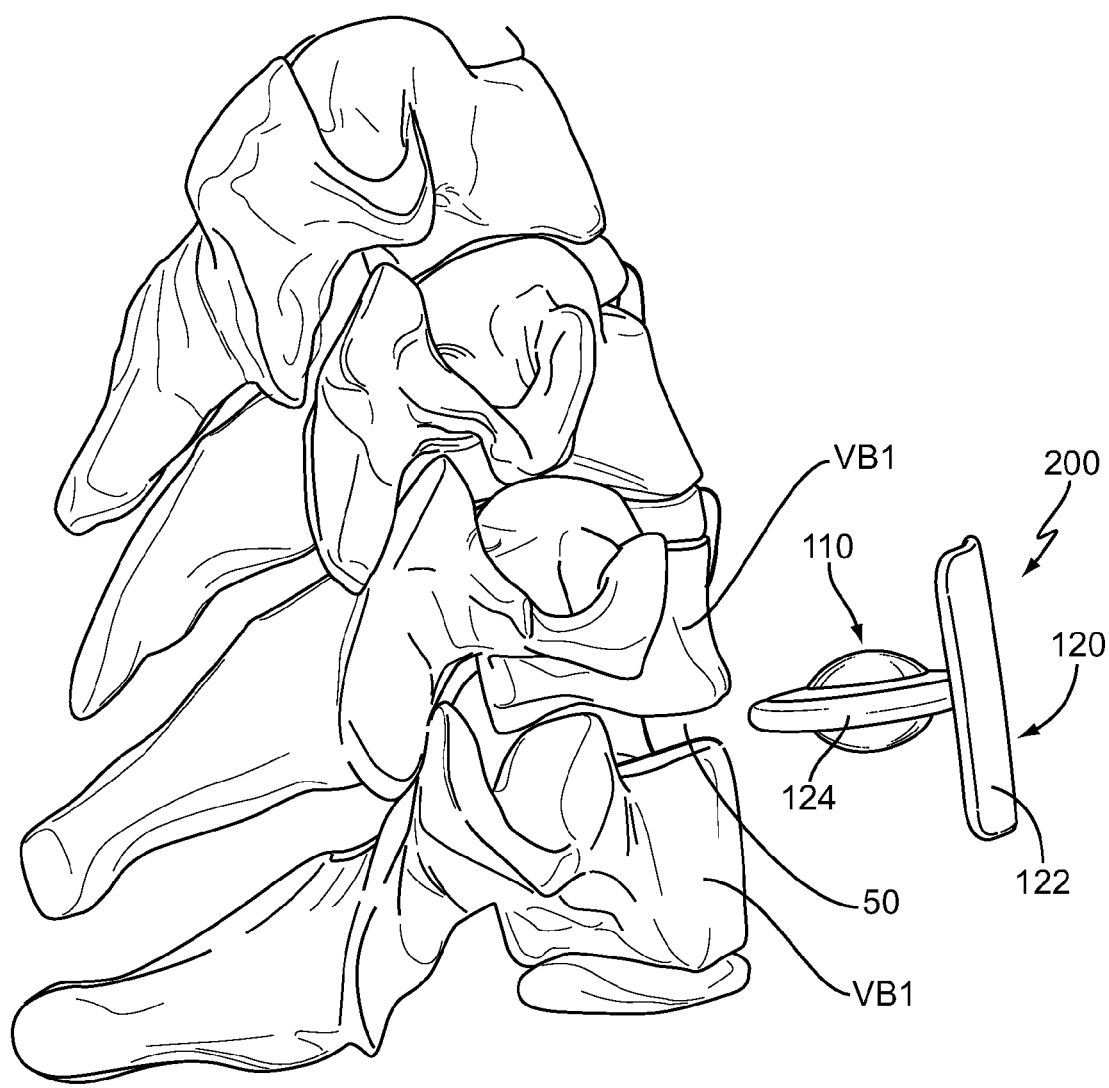
FIG. 7 is an isometric view of a segment of vertebral column the prosthetic disc system of FIG. 5 may be utilized.

FIG. 7 shows a segment of vertebral column, and in particular, where the prosthetic disc system 200 of the present invention may be utilized. Specifically, FIG. 7 shows the disc system 200 just prior to implantation in the disc space 50 between vertebral bodies VB1 and VB2. After a discectomy is performed between vertebral bodies VB1 and VB2, the prosthetic disc system 200 may be implanted so that the nucleus component 110 and tether 124 occupy the resulting disc space 50.

Figure 8:
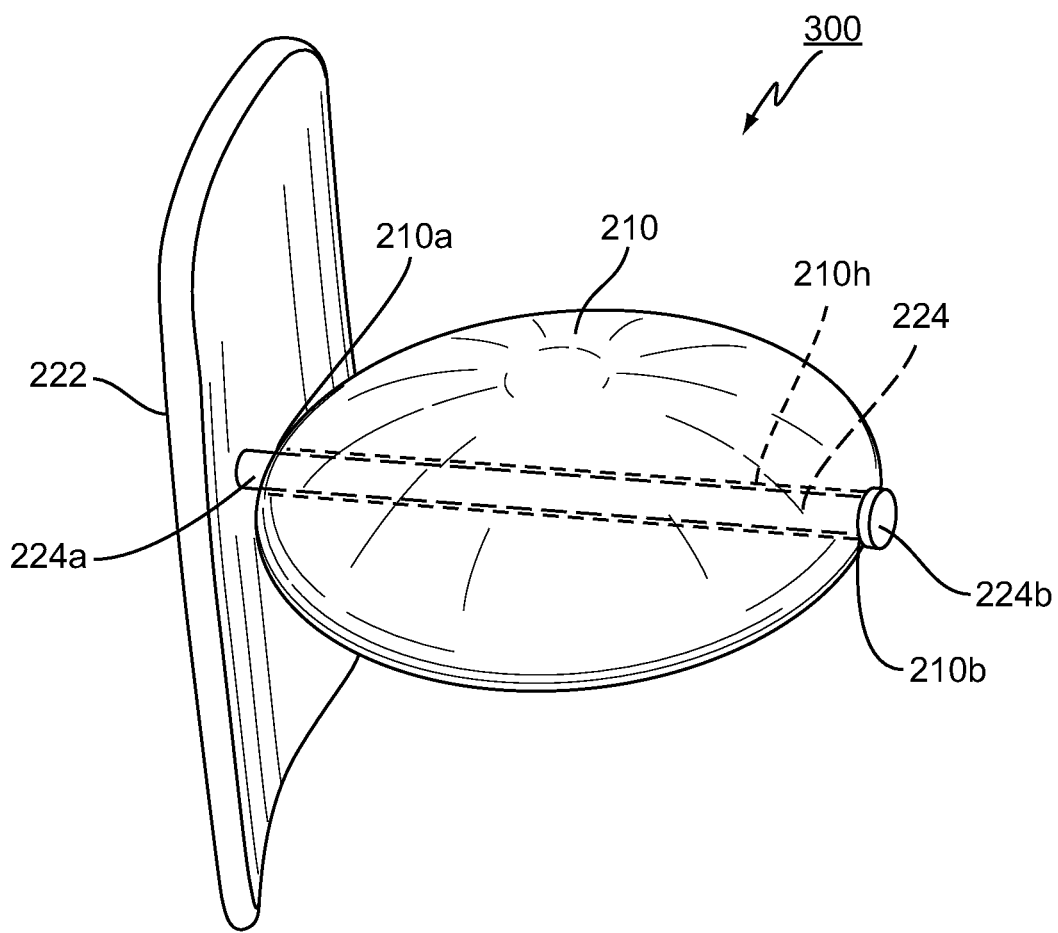
FIG. 8 is an isometric view of another embodiment of a prosthetic disc system of the present invention.

To illustrate the example of a change or alteration of the previously-described embodiments, yet how a different embodiment may fall under the spirit of the invention, shown in FIG. 8 is another embodiment of a prosthetic disc system 300 of the present invention. Specifically, FIG. 8 shows a different form of a tether 224 than those described above. In particular, tether 224 does not span even a majority of the perimeter of the nucleus component 210, but the tether 224 ties the nucleus component 210 to the anchor 222 by extending from the anchor 222, through the nucleus component 210, and maintained in place on part of the nucleus component 210. The nucleus component 210 has a channel or hole 210h extending from a first point 210a on or adjacent the perimeter of the nucleus component 210 that is near the anchor 222 to a second point 210b on or adjacent the perimeter of the nucleus component 210 that is substantially opposite the first point 210a. As shown in FIG. 8, the tether 224 extends from the anchor 222, passed the first point 210a, extends through hole 210h until it reaches the second point 210b.

As shown in FIG. 8, the tether 224 is maintained in place by means of a locking mechanism 224b located at the second point 210b, which may be any mechanism to accomplish this function, for example, the tether 224 may be tied a simple knot. Thus, as shown, the tether 224 is at least partially situated on the perimeter of the nucleus component 210. Even though FIG. 8 shows an embodiment 300 having a different form of a tether 224 than the embodiments 100, 100B, 100C of the prosthetic disc system of the present invention, the same function and benefits of embodiment 100 of, for example, FIGS. 1 and 1A, are present with embodiment 300 of FIG. 8.

Further, additional embodiments in accordance with the present invention do not necessarily necessitate a locking mechanism 224b at the second point 210b. That is, an example of such an embodiment may utilize a nucleus component 210 similar to that of FIG. 8, but also having a channel 12 such as that shown in FIG. 2. In such an embodiment, two separate tethers or two separate parts of a tether may extend from the anchor 222, pass the first point 210a, extend through hole 210h until they reach the second point 210b. At point 210b, each of the two separate tethers or two separate parts of a tether deviate from each other and extend along and extend in the channel until they each reach back at or near first point 210a, thereby bounding the nucleus component by operatively mating with the channel. At first point 210a, the two separate tethers or two separate parts of a tether may be locked in place at or near the first point 210a. For example, at the stage of manufacture when the two separate tethers or two separate parts of a tether meet back at first point 210a, the two separate tethers or two separate parts of a tether may then be pulled taut, thereby pulling the entirety of the tether or tethers taut around the nucleus component, and may be pulled through another hole in anchor 222 at or near the first point 210a. At this time, the entirety of the tether or tethers may be maintained in place with a locking mechanism situated on the side of the anchor 222 opposite the nucleus component. For example, a simple knot or mechanical clip may accomplish such tethering of the nucleus component to the anchor 222.

The nucleus component 110, the anchor 222 and tether 224 of prosthetic disc system 300 can have the same variety in shape and materials as the counterpart features of any of the previously-described embodiments, so long as it accomplishes the same desired functions. For example, tether 224 may be made of braided or woven UHMWPE fabric.

The benefits of the prosthetic disc systems of the present invention and the particular manner in which the nucleus component 10 or 110 is tethered to the anchor 22, are several. Any degree of flexibility in the tether 24, 124 or 224 allows the nucleus component 10, 110 or 210 to move as necessary to achieve physiologic spinal motion, but prevents the nucleus component 10 from migrating beyond desired limits. The manner of tethering allows for a central point of attachment of the nucleus component 10, 110 or 210 to the anchor 22, 122 or 222, i.e., at least with respect to embodiments 100, 100B, 200 and 300, and with similar embodiments according to the present invention where a central point of attachment is present. This central point of attachment (which is the point along the perimeter of the nucleus component 10, 110 or 210 where the tether 24, 124 or 224 is affixed to the anchor 22, 122 or 222) helps with rotation and angular movement of the nucleus component 10, 110 or 210 relative to the adjacent vertebral bodies VB1 and VB2. The particular manner of placing the tether 24 or 224 around the perimeter of the nucleus component 10 or 110, and particularly, with use of the channel 12 or 112 of the nucleus component 10 or 110 allows for a relatively secure affixation of the two parts, while still achieving the movement benefits just described, and particularly, more flexibility and adjustability in the disc system 100 or 200 than existing prosthetic disc systems. Further, the same movement benefits are achieved with the prosthetic disc system 300 of the present invention and its manner of connecting the nucleus component 210 to the anchor 222 by means of its tether 224. Having the tether 24, 124 or 224 primarily (if not solely) situated on the perimeter of the nucleus component 10, 110 or 210, does not subject the tether 24, 124 or 224 (and its material) to heavy wear, limiting the amount of wear debris. For example, if a tether completely surrounded the nucleus component 10, 110 or 210, then such a tether would be subjected to loads from the superior and inferior vertebral bodies and multi-directional forces from them, thereby potentially creating significant wear debris. Over time, that could create more and more wear debris and could damage the tether and its capability to function as intended would be lessened or destroyed.

It is evident that the disc systems of the present invention, and particularly because its need for little or no endplate preparation, provides a prosthetic disc device which decreases patient recovery time, and reduces the occurrence of postoperative degeneration at levels above and below the implant, especially as compared with fusion techniques and particularly, as compared to existing motion-preserving devices. In addition, the disc systems of the present invention maintains proper positioning of the disc (or nucleus component) inside the disc space 50, restores normal disc height and maintains the patient's vertebral lordosis, lessens the chances for post-operative subsidence or expulsion, creates relatively little or no wear debris, and provide elasticity and dampening sufficient to absorb shocks and stresses imposed on it in a manner similar to that of the natural spinal disc.

All adjustments and alternatives described above are intended to be included within the scope of the invention, as defined exclusively in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. Furthermore, as used herein, the terms components and modules may be interchanged. It is understood that all spatial references, such as "superior," "inferior," "anterior," "posterior," "outer," "inner," and "perimeter" are for illustrative purposes only and can be varied within the scope of the disclosure.

The invention claimed is:

1. A prosthetic spinal disc system, the system comprising:
   a nucleus component having an upper surface configured to engage a superior vertebra and a lower surface configured to engage an inferior vertebra, the nucleus component further having a recess extending circumferentially through an outer surface of the nucleus component situated substantially between the upper surface and the lower surface of the nucleus component;
   an anchor comprising a plate having a concave inner surface configured to engage the superior and inferior vertebrae, the anchor extending between a first end configured to engage the superior vertebra and an opposite second end configured to engage the inferior vertebra; and
   a tether comprising a first section having an inner surface and an outer surface and a second section forming at least one leg portion extending transversely from the first section between a first end and a second end, the inner surface of the first section engaging the circumferential recess in the outer surface of the nucleus component, the outer surface of the tether extending a distance past the outer surface of the nucleus, the first end of the at least one leg portion engages the inner surface of the anchor and the second end of the at least one leg portion extends from the tether such that the tether flexibly attaches the anchor to the nucleus component.

2. The disc system of claim 1, wherein the upper surface of the nucleus component has a convex shape.

3. The disc system of claim 2, wherein the lower surface of the nucleus component has a convex shape.

4. The disc system of claim 1, wherein the upper surface of the nucleus component has a convex shape, and the lower surface of the nucleus component has a convex shape.

5. The disc system of claim 1, wherein the nucleus component has a generally elliptical cross-sectional shape in a sagittal plane.

6. The disc system of claim 1, wherein the nucleus component has a generally circular cross-sectional shape in a transverse plane.

7. The disc system of claim 1, wherein the nucleus component has a generally elliptical cross-sectional shape in a sagittal plane and a generally circular cross-sectional shape in a transverse plane.

8. The disc system of claim 1, wherein the nucleus component has, at least in part, a generally circular cross-sectional shape in a sagittal plane.

9. The disc system of claim 1, wherein the nucleus component has a center and an outer portion adjacent the recess, and when viewed in a sagittal plane, the nucleus component has a larger profile in its center than it has at the outer portion.

10. The disc system of claim 9, wherein the nucleus component has a central portion located about the center of the nucleus, and wherein the central portion is harder than the outer portion.

11. The disc system of claim 1, wherein the nucleus component has a central portion and an outer portion adjacent the recess, and wherein the central portion is harder than the outer portion.

12. The disc system of claim 1, wherein the tether comprises flexible material.

13. The disc system of claim 1, wherein the anchor comprises flexible material.

14. The disc system of claim 1, wherein the tether is connected to the anchor at a central location.

15. The disc system of claim 1, wherein the recess is a concavity having a semi-circular cross section.

16. The disc system of claim 1, wherein the anchor and the tether are made from the same material.

17. The disc system of claim 1, wherein the tether includes a radiographic marker.

18. A prosthetic spinal disc system, the system comprising:
    a nucleus component having an upper surface configured to engage a superior vertebra and a lower surface configured to engage an inferior vertebra, the nucleus component further having a recess extending circumferentially through an outer surface of the nucleus component situated substantially between the upper surface and the lower surface of the nucleus component;
    an anchor component comprising a plate having a concave inner surface configured to engage the superior and inferior vertebrae, the anchor extending between a first end configured to engage the superior vertebra or and an opposite second end configured to engage the inferior vertebra; and
    a tether having an inner surface, an outer surface and a second section forming at least one leg portion, wherein the inner surface of the tether is disposed within the circumferential recess in the outer surface of the nucleus component and the outer surface of the tether engages the inner surface of the anchor to flexibly attach the anchor to the nucleus component such that the outer surface of the tether extends a distance past the outer surface of the nucleus component, a first end of the at least one leg portion engages the inner surface of the anchor and a second end of the at least one leg portion engages the tether such that the tether flexibly attaches the anchor to the nucleus component.

19. The disc system of claim 18, wherein the upper surface and the lower surface of the nucleus component are configured to allow for implantation of the disc system, after a discectomy, with no preparation of at least one of the superior and inferior vertebrae.

20. A prosthetic spinal disc system, the system comprising:
a nucleus component having an upper surface configured to engage a superior vertebra and a lower surface configured to engage an inferior vertebra, the nucleus component further having a recess extending circumferentially through an outer surface of the nucleus component situated substantially between the upper surface and the lower surface of the nucleus component;
an anchor comprising a plate having a concave inner surface configured to engage the superior and inferior vertebrae, the anchor extending between a first end configured to engage the superior vertebra and an opposite second end configured to engage the inferior vertebra;
a tether comprising a first section having an inner surface and an outer surface and at least two second sections forming two leg portions each extending transversely from the first section between a first end and a second end, the inner surface of the first section engaging the circumferential recess in the outer surface of the nucleus component, the first end of the two leg portions engages the inner surface of the anchor and the second end of the two leg portions extends from the tether such that the tether flexibly attaches the anchor to the nucleus component.

\* \* \* \* \*